United States Patent [19]

Osborne et al.

[11] 4,161,520

[45] Jul. 17, 1979

[54] METHOD OF TREATING HYPERTENSION

[75] Inventors: Melville W. Osborne, Somerville; Michael R. Cohen, West Orange, both of N.J.

[73] Assignee: Hoffmann-La Roche Inc., Nutley, N.J.

[21] Appl. No.: 731,979

[22] Filed: Oct. 14, 1976

[51] Int. Cl.$^2$ .................... A61K 35/66; A61K 31/35; A61K 31/34
[52] U.S. Cl. .................... 424/115; 424/230; 424/272; 424/274; 424/283; 424/285
[58] Field of Search ............... 424/283, 285, 230, 272, 424/274, 115

[56] References Cited

U.S. PATENT DOCUMENTS

| | | | |
|---|---|---|---|
| 3,715,372 | 2/1973 | Stempel et al. | 424/115 |
| 3,873,715 | 3/1975 | Pressman et al. | 424/283 |
| 3,985,893 | 10/1976 | Holland et al. | 424/272 |

Primary Examiner—Sam Rosen
Attorney, Agent, or Firm—Jon S. Saxe; Bernard S. Leon; Frank P. Hoffman

[57] ABSTRACT

A method is disclosed for treating hypertension in warm-blooded animals by the oral administration, to an animal in need of such treatment, of a therapeutically effective dose for example, from about, 0.1 to 5 mg/kg/day as chronic administration or 5 to 10 mg/kg/day, of a polyether compound such as bromolasalocid or bromoisolasalocid. Also disclosed are examples of such polyether compounds and methods for their preparation.

20 Claims, No Drawings

METHOD OF TREATING HYPERTENSION

BACKGROUND OF THE INVENTION

Hypertension is a widespread circulatory disease which afflicts millions of warm-blooded animals. It is manifested by high blood pressure and is accompanied by a loss of elasticity (compliance) of the arteries. The causes of some hypertensive conditions are not known, i.e., in cases of essential hypertension. Other types of high blood pressure are caused by specific diseases, e.g., primary aldosteronism, aortic coarctation, renal stenosis, and pheochromocytoma.

To date, many chemotherapeutic agents are used to treat hypertension. Their effects are maintained by either venous expansion, i.e., reducing venous return to the heart and causing a lowering of arterial blood pressure, or by static arterial vasodilation. None of the agents presently in use treat the disease per se, they only treat the symptoms, which symptoms return quickly upon cessation of treatment.

There is thus a need for an agent which reduces arterial blood pressure and meets the following criteria:
(a) increases compliance of the blood vessels
(b) has essentially no effect on the heart rate
(c) is orally absorbed
(d) is effective in small doses with infrequent administration
(e) has a good therapeutic index
(f) has no significant diuretic action
(g) treats the disease rather than the symptoms only
(h) causes no manifestations of cardiovascular compensation
(i) is not effective by action on the nervous system
(j) does not cause a venous pooling, and
(k) can be combined with known antihypertensive agents.

According to this invention it has been discovered that pharmaceutical compositions containing an effective antihypertensive amount of, as the active agent, a compound characterized by being a naturally occurring polyether ionophore, or derivatives of such compounds, will fulfill the criteria set forth above.

Polyether ionophores are compounds which facilitate the transport of monovalent or divalent cations across a membrane. The "polyether" nature of the ionophore refers to the considerable number of tetrahydro-pyrans and -furans found in the ionophore structure. For the most part, these compounds have been found to exhibit weak antibiotic activity. Other utilities for many of these compounds include activities as growth promotants (U.S. Pat. No. 3,839,557), coccidiostatic agents (U.S. Pat. Nos. 3,719,753 and 3,577,531) and cardiovascular agents (U.S. Pat. No. 3,873,715).

Pressman et al., discoverers of the therapeutic effect of certain of the polyether ionophores as cardiovascular agents, determined that significant changes in myocardial force of contraction, heart rate and blood pressure could be achieved following intravenous injection of certain polyether ionophores. Pressman et al. found that cardiac output, blood pressure, stroke volume and contractile force were all substantially increased by intravenous administration of selected polyether ionophores. It was therefore unexpected and surprising to find that chronic oral administration of polyether ionophores at low dosage levels, when compared to cardiotonic active amounts, produced a significant decrease in arterial blood pressure in warm-blooded hypertensive animals with concomitant changes in the hemodynamic profile toward the normal state.

With or without a lowering of arterial blood pressure, cardiovascular diseases, such as angina, claudication and decreased blood flow to the brain would be expected to be positively affected, by chronic administration at low dosage levels of the disclosed polyether ionophores. This is due to the fact that arterial blood flow is enhanced by decreasing pulse wave velocity secondary to increasing compliance so that blood flow is now regulated by a normal physiologic mechanism, i.e., a pressure gradient (potential energy) rather than kinetic energy.

Thus, another utility of the present compounds would be in the treatment of warm-blooded animals which are not hypertensive but who manifest cardiovascular diseases such as discussed above.

The following compilation represents typical polyether compounds which exhibit an ionophoric effect and are useful in treating hypertension and in reverting the hemodynamic profile to a normal state. The formulas which follow utilize the shorthand notations Me and Et which represent methyl and ethyl, respectively.

Monovalent Compounds

| Compound Name | Formula |
| --- | --- |
| Nigericin | (structure shown) |

Nigericin has been known for some time under the names helixin C, antibiotic X-464, antibiotic K-178, polyetherin A, and azalomycin M. Its structure was characterized by Steinrauf et al., Biochemical and Biophysical Research Communications 33, 29 (1968). Harnes et al., Antibiotic and Chemotherapy I, 594–96 (1951) originally mentioned nigericin. It was also described by Gorman et al. in U.S. Pat. No. 3,555,510.

The organism which produces nigericin is a strain of *Streptomyces violaceoniger* which is on unrestricted deposit under identification number NRRL B1356 in the Northern Research and Utilization Development Division, Agricultural Research Service, U.S. Department of Agriculture, Peoria, Ill. The preparation of nigericin is described in U.S. Pat. Nos. 3,794,732 and 3,839,557.

| | |
|---|---|
| Monensin | $R_1$ = CH(Me)CO$_2$H, $R_2$ = Me, $R_3$ = Et. |
| Factor B | $R_1$ = CH(Me)CO$_2$H, $R_2$, $R_3$ = Me |
| Factor C | $R_1$ = (CH$_2$)$_3$CO$_2$H, $R_2$ = Me, Me |
| Factor D | $R_1$ = CH(Me)CO$_2$H, $R_2$ = Et, $R_3$ = Me |

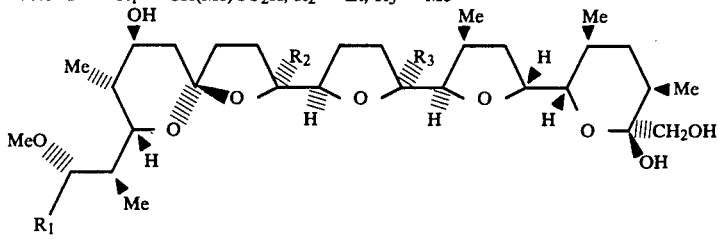

Monensin was described by Haney et al., U.S. Pat. No. 3,501,568. The substance commonly known as monensin or A 3823 complex is actually a mixture of four components. These four components are included in the term "monensin" as used herein.

Monensin is the fermentation product of an organism

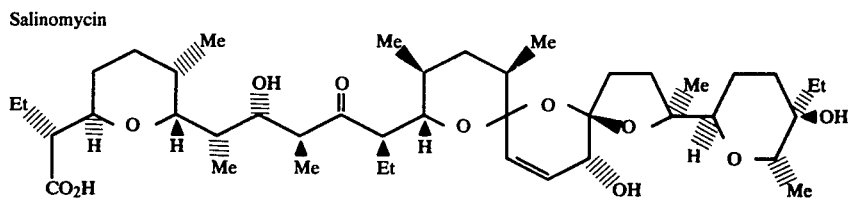

which can be found on unrestricted deposit under the number ATCC 15413 in the American Type Culture Collection, Rockville, Md. A method of production for the monensin complex is disclosed in U.S. Pat. No. 3,501,568.

Also within the ambit of the present invention are the metabolites of monensin such as A-27106 disclosed and claimed in U.S. Pat. No. 3,932,619. A-27106 is produced from the conversion of monensin by an enzyme system produced by an organism Streptomyces candidus available as accession number NRRL 5449 at Northern Regional Research Laboratories, Peoria, Ill.

ter for Information on Antibiotics) Liege, Belgium, which lists the organism on page 31 of its Bulletin No. 3 (1966). Its formula has been characterized by Blount et al., Chemical Communications (London), p. 533, 1975. A method for the preparation of X-206 is disclosed in U.S. Pat. Nos. 3,794,732 and 3,839,557.

The compound Salinomycin was first reported in 1973 by Kinahsi et al., Tetrahedron Letters, 49, 4955 (1973). Salinomycin is the fermentation product of an organism (Streptomyces Albus) which can be found on unrestricted deposit under Number ATCC 21838 in the American Type Culture Collection, Rockville, Md. and from the Fermentation Research Institute in Japan as Streptomyces Albus 80,614 (No. 419). A method of producing Salinomycin by fermentation is disclosed by Tanaka et al. in U.S. Pat. No. 3,857,948.

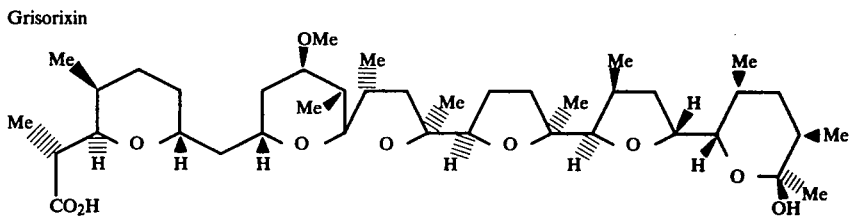

The compound Grisorixin was first reported in 1970 by Gachon et al., Chem. Commun., P 1421 (1970). The

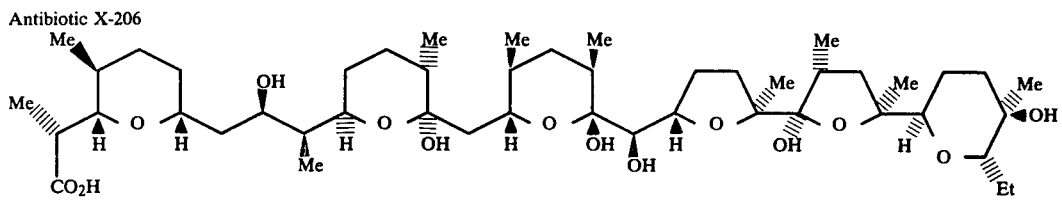

The compound X-206 was reported for the first time in 1951 by Berger et al., JACS 73, 5295-98 (1951). The Streptomyces organism from which one is able to obtain antibiotic X-206 is available at Center International d'Information sur Les Antibiotiques (International Cencompound was found to differ by only a single oxygen atom from nigericin. The Streptomyces organism from which one is able to obtain the compound Grisorixin is Streptomyces griseus. A method for the preparation of Grisorixin is shown in the Gachon et al. article. The organism is on deposit at the Institut National De la Recherche Agronomique assigned the designation INRA SAB 2142.

Laidlomycin

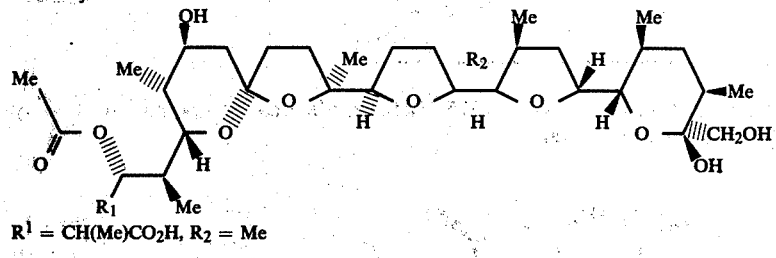

$R^1 = CH(Me)CO_2H$, $R_2 = Me$

The compound "laidlomycin" and a method for its production has been disclosed by Kitame et al. in the Journal of Antibiotics, Vol. XXVII No. 11, pp. 884–888, 1974. The compound is produced by the fermentation of a Streptomyces eurocidicus var. asterocidicus (similar) assigned the designation Streptomyces S-822. The species is indexed as S-822 at the Department of Bacteriology, Tohoku University School of Medicine, Sendai, Japan.

tion product of an organism (*Streptomyces hygroscopicus*) which can be found on unrestricted deposit under number NRRL 3444 in the Northern Research and Utilization Development Division, Argicultural Research Service, U.S. Department of Agriculture, Peoria, Illinois. A method for its preparation is disclosed in U.S. Pat. No. 3,577,531 to Gorman et al.

Antibiotic A-130A
(Ro 21-6150)

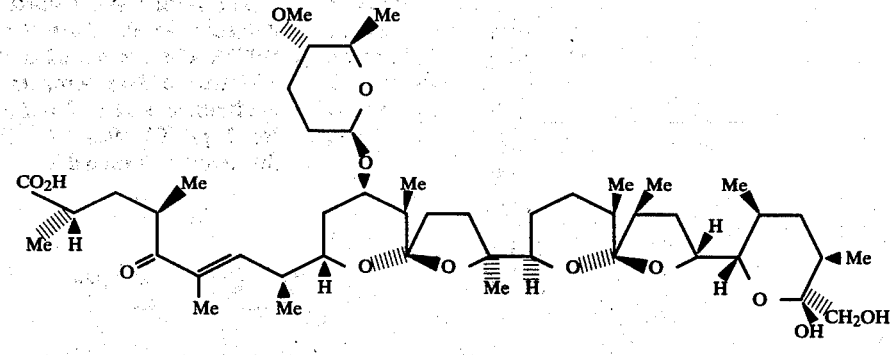

The compound A-130A was discovered by Oikawa et al. and is disclosed together with a method for its production in U.S. Pat. No. 3,903,264 issued Sept. 2, 1975. The compound is produced by the fermentation of a strain of Streptomyces hygroscopicus available to the public under the accession number ATCC 21840 at the American Type Culture Collection in Rockville, Md.

Recently, Blount et al. in Chemical Comm. (London),

Monovalent (monoglycoside) Compounds

| Compound Name | Formula |
|---|---|
| Dianemycin | |

The compound Dianemycin was first reported in 1971 by Czerwinski et al., Biochem. Biophys. Res. Commun., 45, 1284 (1971). Dianemycin is the fermentapp. 853–855 (1975) have provided a structural elucidation of this compound.

A 28086
Factor A ($R_1 = R_2 = Me$, $R_3 = OH$)
Factor B ($R_1$, $R_2 = Me$; $R_3 = O$)
Factor D ($R_1$, $R_2 = Me$, Et; $R_3 = OH$)

-continued

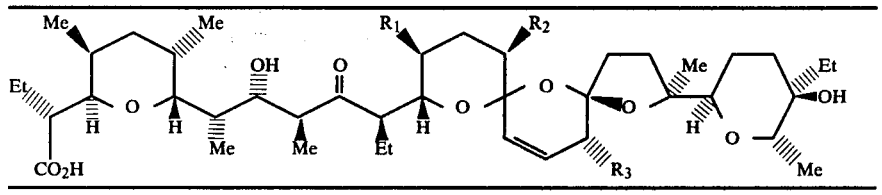

Antibiotic complex A 28086 is made up of at least three components, one of which, factor A, is known as narasin. The complex is produced by fermentation of an organism, Streptomyces aureofociens which can be found on deposit at the Northern Regional Research Laboratories in Peoria, Ill. under NRRL numbers 8092 or 5758. A method of fermentation to produce the A 28086 complex is disclosed in Belgium Pat. No. 830,043 published Dec. 10, 1975.

Alborixin

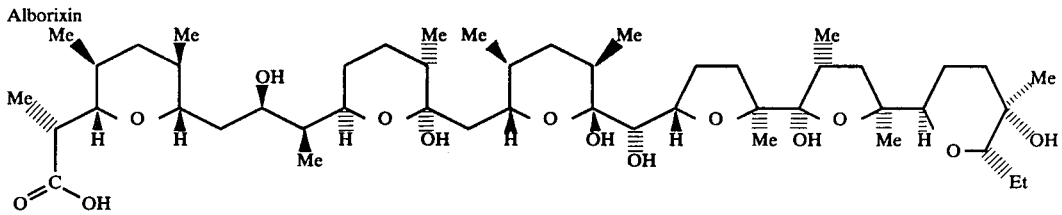

The compound Alborixin was first reported by M. Alleaume et al., Chem. Comm. (London), pp 411–412 (1975). The compound is obtained by the fermentation of a strain of Streptomyces albus sp. 3840 as reported by Delhomme et al. in Journal of Antibiotics, Vol. XXIX, No. 7, pp 692–695 (1976). The organism is on deposit at the Institut National De La Recherche Agronomique Lonomycin
(TM - 481)

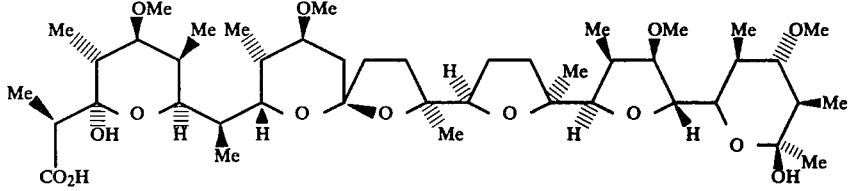

The antibiotic lonomycin was first reported and elucidated structurally by Omura et al. in Journal of Antibiotics, Vol. XXIX, No. 1, pp 15–20, Jan. 1976 and Otake et al., Tet. Letters No. 47, pp. 4147–4150, 1975. The antibiotic is produced by a Streptomyces ribosidificus strain TM-481 which is deposited as ATCC No. 31051 at the American Type Culture Collection in Rockville, Md. A method of producing the antibiotic by fermentation is disclosed by Sawada et al. in U.S. Pat. No. 3,950,514. Subsequent publications by Riche et al. (as Emericid) in Chem. Comm. (London), pp 951–952 (1975) and Benazet et al. (as 31599 RP) at the 9th International Congress of Chemotherapie in London, July 13–18, 1975 disclosed identical compounds to lonomycin.

assigned the designation INRA SAB 3840.

Septamycin

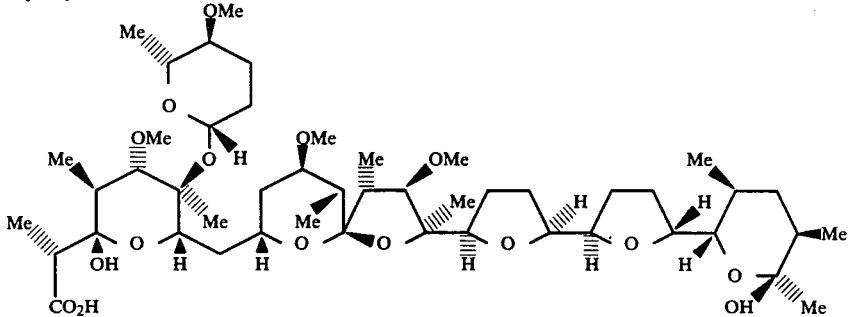

The compound Septamycin also known as A 28695 together with A 28695B was first described in U.S. Pat. No. 3,839,558 to Hamill et al. The structure was elucidated by T. J. Petcher et al., Chem. Comm., 697 (1974). Septamycin differs from A-204A (below) in the loss of one of the five methoxyls present in A-204A and a change in the configuration and the point of attachment of the glycoside-like branched tetrahydropytonyl ring. Septamycin is obtained by the fermentation of a strain of Streptomyces hydroscopicus as disclosed in the above mentioned patent.

disclose information on the above antibiotic which is disclosed as a complex.

Antibiotic A-204A

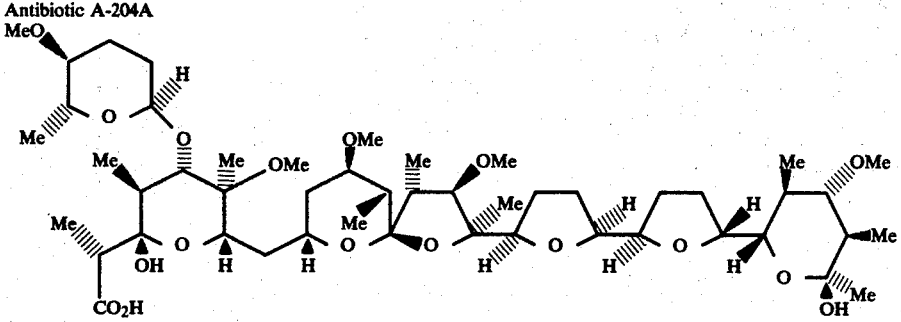

The compound A-204A was reported for the first time by N. D. Jones et al., J. Amer. Chem. Soc., 95, 3399 (1973). It is obtained by the fermentation of a strain of the organism Streptomyces albus. This strain is found on unrestricted deposit under the number NRRL 3384 in the Northern Research and Utilization Development Division, Agricultural Research Service, U.S. Department of Agriculture, Peoria, Ill. A method for the production of A-204A (I) is disclosed in U.S. Pat. No. 3,705,238. U.S. Pat. Nos. 3,953,474 and 3,907,832 also Antibiotic 38295

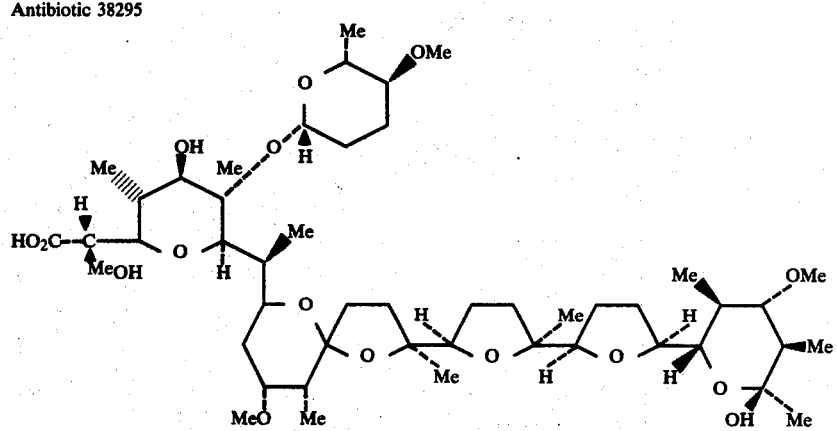

The compound antibiotic 38295 was first reported by Celmer et al. in Belgium Pat. No. 831,947 published on Feb. 2, 1976. The patent discloses a method of production for the antibiotic by fermentation of the organism Streptomyces hygroscopicus found on deposit under the number ATCC 31050 in the American Type Culture Collection, Rockville, Md.

Lasalocid A  $R_1=R_2=R_3=R_4=Me$
Lasalocid B  $R_1=Et, R_2=R_4=Me$
Homolog C  $R_2=Et, R_1=R_3=R_4=Me$
D  $R_3=Et, R_1=R_2=R_4=Me$
E  $R_4=Et, R_1=R_2=R_3=Me$

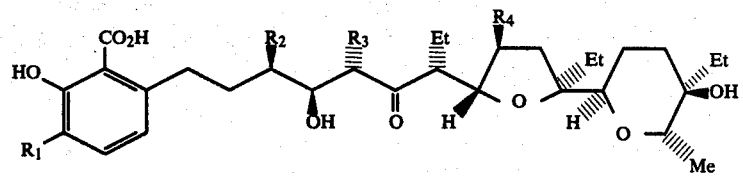

Iso-Lasalocid A

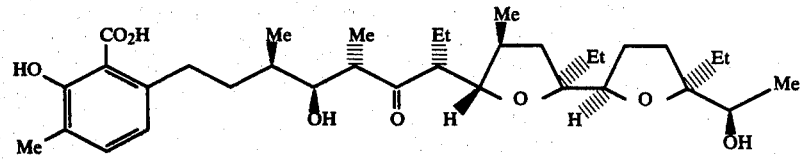

The compound Lasalocid A, its isomer and its homologs are produced by the fermentation of the organism Streptomyces lasaliensis. The organism can be found on unrestricted deposit under the number NRRL 3382 in the Northern Research and Utilization Development Division, Agricultural Research Service, U.S. Department of Agriculture, Peoria, Ill. and under the number ATCC 31180 in the American Type Culture Collection, Rockville, Md. The compound Lasalocid A, its isomer and its homologs have been first reported by Berger et al., J. Amer. Chem. Soc., 73 5295 (1951), J. Westley et al., J. Antibiot., 27, 597 (1974) and J. Westley et al., J. Antibiot., 27, 744 (1974) respectively. Also disclosed in these articles are methods for the preparation of the respective compounds.

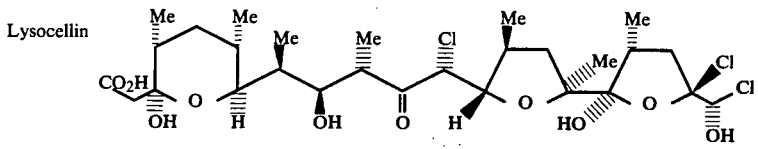

Lysocellin

The compound Lysocellin was first reported by E. Bata et al. in J. Antibiotic., 28, 118–121 (1975). The compound is produced by fermentation of a Streptomyces cocaoi var. asoensis K-9 Met. mutant. It has also been found this compound, also known as X-14537A, can be produced by fermentation of a Streptomyces longwoodensis var. longwoodensis which is deposited as ATCC 20251 at the American Type Culture Collection in Rockville, Md. and the fermentative method disclosed in Int. J. of Systematic Bacteriology, Vol. 26 (3), pp 319–322, 1976 article by Palleroni et al.

Divalent Pyrrole-Ether Compounds

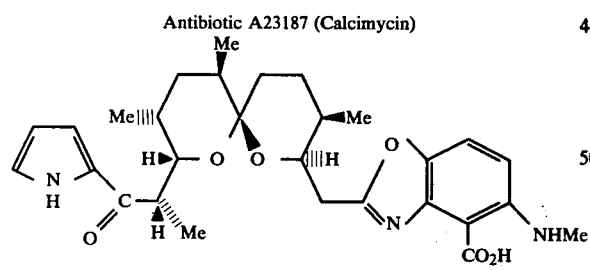

Antibiotic A23187 (Calcimycin)

The compound A 23187 was first reported by M. O. Chaney et al., J. Amer. Chem. Soc., 96, 1932 (1974) as containing two cyclic ethers in a spiro ring system and a carboxylic acid function. The molecular formula was calculated as $C_{29}H_{37}N_3O_6$. The compound is obtained by the fermentation of a strain of Streptomyces chartreusensis. A method of preparation of A 23187 by fermentation of the Streptomyces chartreusensis is set forth in U.S. Pat. No. 3,923,823 to Gale et al. The organism is on deposit at the Northern Regional Research Laboratories, Peoria, Ill. as NRRL 3882.

Antibiotic X-14547A

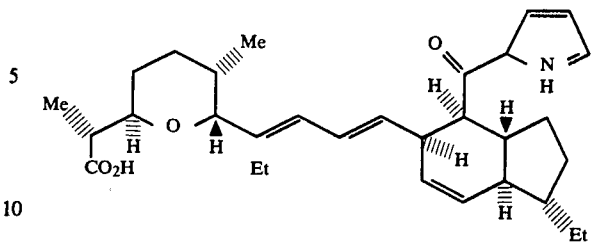

The compound X-14547A is produced by the fermentation of a novel strain of Streptomyces sp. X-14547 which is deposited at Northern Regional Research Laboratories, Peoria, Ill. as NRRL 8167.

The Antibiotic X-14547 A producing culture is grown and maintained on a starch-casein agar slant having the following composition (grams/liter distilled water);

| | |
|---|---|
| Soluble starch | 10.0 |
| Casein | 1.0 |
| $K_2HPO_4$(anhydrous) | 0.5 |
| $MgSO_4$(anhydrous) | 0.5 |
| Agar | 20.0 |

Adjust pH to 7.4 with NaOH before autoclaving at 15–20 pound pressure for 20 minutes.

The slant is inoculated with Antibiotic X-14547 A producing culture (Streptomyces X-14547) and incubated at 28° C. for 7–10 days. A chunk of agar from the sporulated culture is then used to prepare vegetative inoculum by inoculating a 6-liter Erlenmeyer flask containing 2 liters of inoculum medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$(anhydrous) | 1.0 | pH is adjusted to 7.0 before autoclaving at 15–20 pound pressure for 45 minutes.

The inoculum medium is inculated for 72 hours at 28° C. on a rotary shaker operating at 250 rpm.

Four liters of this culture are used to inoculate 60 gallons of the following medium in a 100 gallon fermentor (grams/liter tap water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$(anhydrous) | 1.0 |
| Sag 4130 Antifoam | |

| | |
|---|---|
| -continued | |
| (Union carbide) | 0.1 |

The pH of the medium is adjusted to 7.0 with NaOH before sterilization for 1¼ hours with 60 lb.²/in steam.

The inculated medium is aerated with compressed air at a rate of 3 cubic feet per minute and is stirred with agitators at 280 rpm. The fermention is carried out at 28° C. for 43 hours.

Five gallons of this culture are used to inoculate 350 gallons of the following medium in a 1000 gallon tank utilizing the following medium (grams/liter tap water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| CaCO₃ | 1.0 |
| K₂HPO₄(anhydrous) | 1.0 |
| Sag 4130 Antifoam (Union carbide | 0.1 |

The pH of the medium is adjusted to 7.0 with NaOH before sterilization for 1¼ hours with 60 lb.²/in steam.

The inoculated medium is aerated with compressed air at a rate of 3 cubic feet per minute and is stirred with agitators at 280 rpm. The fermentation is carried out at 28° C. for 118 hours.

To the whole broth from a 350 gallon (1350 liters) fermentation as set forth above of Streptomyces sp. X-14547, was added, after 118 hours of growth, an equal volume of ethyl acetate. After stirring for one hour the solvent layer was separated and concentrated to 7.25 liters under reduced pressure. The concentrated solvent extract was washed with 3 liters of 1N HCl three times. The solvent was dried over Na₂SO₄ and concentrated to an oil under reduced pressure. The oil was dissolved in diethyl ether and crude pyrrole-2-carboxylic acid crystals were separated by filtration. Recrystallization from ethanol/ether yielded the analytical sample of the above compound: mp 202°–203° C.

microanalysis: calcd %C, 54.06; %H; 4.54; %N, 12.60. found %C, 54.33; %H, 4.65; %N, 12.60.

The mother liquor was concentrated to an oil under reduced pressure, redissolved in 1 liter of acetonitrile and washed twice with equal volumes of n-hexane. The hexane washes were pooled and extracted with ½ volume of methanol. The methanol extract was pooled with the acetonitrile and the solvent removed under reduced pressure. The oily solid was dissolved in acetonitrile and after cooling to approximately 3° C. overnight crystalline antibiotic X-14547A was recovered upon filtration as a hemihydrate, mp 137° C., $[\alpha]_D$ −285° (C., 1 in CHCl₃).

Microanalysis: calcd for $C_{31}H_{43}NO_4 \cdot (H_2O)_{0.5}$ (502.70): %C, 74.07; %H, 8.92; %N, 2.78; %O; 14.32. found: %C, 74.36; %H, 8.93; %N, 2.50; %O, 13.81.

Polyether Ionophore Compounds of Unknown Structure

Ionomycin

Ionomycin is disclosed in U.S. Pat. No. 3,873,693 to Meyers et al. The compound is obtained by fermentation of an organism Streptomyces conglobatus deposited as ATCC 31005 at the American Type Culture Collection, Rockville, Md. Characterization of the compound by I.R. and U.V. spectra are disclosed in the patent.

Antibiotic BL 580α and β

Antibiotics BL 580α and β are disclosed in U.S. Pat. No. 3,812,249 to Martin et al. The compounds are obtained by fermentation of an organism Streptomyces hygroscopicus deposited as NRRL 5647 at the Northern Regional Research Laboratories. Peoria, Ill. IR spectra of the two antibiotics are disclosed in the patent.

K-41

The compound "K-41" and a method for its production has been disclosed by Tsuzi et al. in the Journal of Antibiotics, Vol. XXIX No. 1, pp 10–14, 1976. The compound is produced by the fermentation of a Streptomyces hygroscopicus given the designation FERM-P 1342 and on deposit at the Fermentation Research Institute, agency of Industrial Science and Technology, Chiba, Japan.

Considered within the ambit of the present invention are the organic or inorganic pharmaceutically acceptable salts of the polyether compounds. These salts are prepared from the free acid by methods well known in the art, for example, for washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like, alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonate and sulfates. Preferred for use in this invention are salts formed from alkali metal bases.

Examples of organic bases forming pharmaceutically acceptable salts with the polyether compounds are lower alkyl amines, primary, secondary and tertiary hydroxy-lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility which makes them amenable to parenteral use.

Also considered within the ambit of the present invention are the derivatives of the polyether compounds Lasalocid A, its isomers and homologs. Disclosure of these derivatives and teaching of their preparation and identify may be found, for example, in U.S. Pat. No. 3,715,372 issued Feb. 6, 1973, U.S. Pat. No. 3,944,573 issued Mar. 16, 1976 and U.S. Pat. No. 3,836,516 issued Sept. 17, 1974. These patents are herewith incorporated by reference for completeness of disclosure in the present application.

For use as antihypertensive agents, the active agents are formulated, using conventional inert pharmaceutical adjuvant materials, into dosage forms which are suitable for oral administration. Other dosage forms, e.g., parenteral, may be possible. The oral dosage forms include tablets, capsules, dragees, suspensions, solutions and the like. The identity of the inert adjuvant materials which are used in formulating the active ingredients into oral dosage forms will be immediately apparent to persons skilled in the art. These adjuvant materials, either inorganic or organic in nature, include, for example, gelatin, albumin, lactose, starch, magnesium stearate, preservatives (stabilizers), melting agents, emulsifying agents, salts for altering osmotic pressure, buffers, etc., which can be incorporated, if desired, into such formulations.

It has been found that subacute oral administration of the active ingredient, i.e., dosing up to five (5) days with discontinuance thereafter, in a warm-blooded animal, e.g., the DOCA Na. hypertensive rat, is most effective when the dose level is within the range of about 5 mg/kg/day to about 100 mg/kg/day, more preferably about 5/mg/kg/day to about 10 mg/kg/day. Chronic oral administration of the active ingredient, i.e., dosing over five (5) days, is most effective when a low dose level is utilized, i.e., less than 0.1 mg/kg/day, e.g., 0.01 mg/kg/day to about 5 mg/kg/day. The above dosage regimens may also be utilized when treating other cardiovascular problems as alluded to previously, i.e., in reverting the hemodynamic profile to a normal state.

Of the above dosage regimens, most preferred is the chronic low level administration of the active ingredient, i.e., less than 0.1 mg/kg/day to about 5 mg/kg/day. The dosage administered to a particular individual should be varied within the above dosage range, based on the toxicity of the particular polyether ionophore. The desired antihypertensive effect must be a function of the particular compound's potency, and the weight and physical condition of the individual patient. Therefore, an effective dosage amount of active compound can only be determined by the clinician utilizing his best judgment on the patient's behalf.

The antihypertensive effects of the active agents are confirmed in both spontaneous hypertensive or DOCA Na. hypertensive rats.

The following examples illustrate the invention.

EXAMPLE 1

A test was conducted for antihypertensive activity in the DOCA Na rat. DOCA rats weighing 170 to 210 grams are used in the test. DOCA Na hypertension is induced by unilateral nephrectomy followed by subcutaneous implantation of a 25 mg. desoxycorticosterone (DOCA) pellet. Animals are placed in individual cages receiving 0.9% sodium chloride solution to drink and rat chow diet ad libitum. Two weeks are allowed to elapse from the time of surgery for development of hypertension, i.e., systolic blood pressure of at least 150 mmHg.

Systolic blood pressure and heart rate are measured indirectly from the tail pressure pulse of unanesthetized rats, using a pneumatic pulse transducer. Control readings are taken prior to drug and post drug readings are taken at 1, 3, 6 and 24 hours.

The experimental results are represented as absolute values. Drug-related alterations in systolic blood pressure are expressed as percentage change by comparing control absolute values with post drug absolute values. Compounds are considered active when about a 15% or greater reduction in blood pressure is obtained. However, the reduction in blood pressure must show mathematical significance ($p < 0.5$).

A derivative of the polyether ionophore, lasalocid, i.e., the bromo derivative of lasalocid, was tested in the above screen. The compound was orally administered for a five-day period by intubation and thereafter dosing was discontinued but blood pressure monitoring was continued. The following table illustrates the results obtained utilizing bromolasalocid as the test drug.

TABLE I

| Oral Dose mg/kg Per Day For 5 Days | No. of Rats in Group | Average Systolic Blood Pressure (mmHg) Per Group | | | | | | | | | |
|---|---|---|---|---|---|---|---|---|---|---|---|
| | | Day 1 | | Day 2 | | Day 3 | | Day 4 | | Day 5 | |
| | | am | pm | am | pm | am | pm | am | pm | am | pm |
| 5 | 6 | 209 | 193 | 206 | 194 | 204 | 191 | 206 | 201 | 197 | 196 |
| 10 | 12 | 217 | 192* | 181* | 166* | 171* | 163* | 173* | 157* | 176* | 166* |

*$p < .05$
The Day 1 a.m. blood pressure readings are the pre-drug controls.

Blood pressure remained below control for a ten (10) day period after drug dosing for the first five consecutive days.

EXAMPLE 2

Test conducted for effects on blood pressure in the spontaneous hypertensive (SH) rat.

Twelve week old spontaneous hypertensive male rats (Okomoto strain) are used as a model in the antihypertensive test.

Systolic blood pressure is measured indirectly from the tail of unanesthetized rats using a pneumatic pulse transducer. Control readings are taken prior to drug administration and post drug readings are taken at 1, 3, 6 and 24 hours.

Drug-related alteration in systolic blood pressure is expressed as percentage change by comparing control absolute values with post drug absolute values.

The results are expressed as absolute values and percent changes from controls.

Compounds are considered active when about a 15% or greater reduction in blood pressure is obtained. However, the reduction in blood pressure must show mathematical significance ($p < 0.5$). The compound was administered for a five-day period by intubation and thereafter dosing was discontinued but blood pressure monitoring was continued.

Table II shows the results obtained in the spontaneously hypertensive rat model using bromolasalocid as the representative antihypertensive polyether compound.

TABLE II

| Dose mg/kg per day For 5 Days | No. of Rats in Total Group | Average Systolic Blood Pressure (mmHg) Per Group | | | | | | | | | | | |
|---|---|---|---|---|---|---|---|---|---|---|---|---|---|
| | | Day 1 | | Day 2 | | Day 3 | | Day 4 | | Day 5 | | Day 8 | |
| | | am | pm | am | pm | am | pm | am | pm | am | pm | am | pm |
| 10 | 6 | 227 | 211* | 215 | 217 | 203* | 199* | 193* | 198* | 200* | 209* | 199* | — |
| 20 | 6 | 211 | 201 | 209 | 200 | 214 | 209 | 205 | 204 | 210 | 187* | 210 | — |
| 50 | 6 | 215 | 208 | 193* | 176* | 175* | 160* | 183* | 169* | 184* | 167* | 207 | — |

TABLE II-continued

| Dose mg/kg per day For 5 Days | No. of Rats in Total Group | Average Systolic Blood Pressure (mmHg) Per Group | | | | | | | | | | |
|---|---|---|---|---|---|---|---|---|---|---|---|---|
| | | Day 1 | | Day 2 | | Day 3 | | Day 4 | | Day 5 | | Day 8 |
| | | am | pm | am | pm | am | pm | am | pm | am | pm | am | pm |
| 100 | 6 | 218 | 176* | 185* | 142* | 128* | 123* | 113* | 131* | — | 108* | — | — |

*$p<.05$
Day 1 a.m. blood pressure readings are the pre-drug controls.

EXAMPLE 3

Using bromolasalocid as a standard for comparison, a number of polyether ionophores were tested for antihypertensive activity. The tests were conducted utilizing single oral dosages in the DOCA-Na. rat over a five-day period with dosing discontinued thereafter. Blood pressure monitoring was carried out for the five-day period and daily after cessation of dosing until blood pressure returned to pre-drug levels. The ionophores tested were of diverse structure and had a wide range of oral toxicities. The daily dosage was calculated by using one-one hundredth (1/100) of the oral (per os) toxicity ($LD_{50}$) up to a maximum of 10 mg/kg/day. The antihypertensive activity expressed as AHR (Subacute antihypertensive ratio) was calculated using bromolasalocid as the standard reference (Table III). From these results, it is apparent that differences exist in onset and duration of antihypertensive activity and potency but that all of the tested compounds exhibit antihypertensive activity.

TABLE III

| NAME | MG/KG $LD_{50}$ | AHR* | ONSET TO MAX. RESPONSE (DAY) | DURATION OF EFFECT (DAYS) |
|---|---|---|---|---|
| X-206 | 17 | 28.3 | 3 | 9 |
| NIGERICIN | 190 | 4.0 | 3 | 9 |
| MONENSIN | 250 | 7.2 | 2 | 9 |
| BROMOLASA-LOCID | 1200 | 1.0 | 4 | 15 |
| BROMOISOLA-SALOCID | >1000 | 0.85 | 2 | 8 |
| A-23187 | >1000 | 0.93 | 4 | 10 |
| A-204 | 14 | 86.6 | 4 | 5 |
| A-130A | 55 | 1.47 | 3 | 7 |
| X-14547A | 129 | 0.58 | 2 | 3 |
| LYSOCELLIN | 225 | 2.08 | 2 | 3 |
| BL-580 | 14 | 6.9 | 4 | 18 |

*AHR (Subacute antihypertensive ratio) = 
$\frac{\Delta \text{Antihypertensive Response/Dose (Test Compound)}}{\Delta \text{Antihypertensive Response/Dose (Bromo Lasalocid)}}$ The following represents tablet and capsule formulations which may be utilized to administer the required dosage of active ingredient. Although bromolasalocid, a preferred compound of the present invention, is utilized in the following examples, it should be recognized that all of the compounds disclosed in the specification as being useful may be substituted therefor.

CAPSULE FORMULATION

| | mg/cap | mg/cap | mg/cap | mg/cap |
|---|---|---|---|---|
| 1. Bromolasalocid | 0.1 | 1.0 | 5.0 | 10.0 |
| 2. Polyvinylpyrrolidone | 20.0 | 20.0 | 20.0 | 20.0 |
| 3. Modified Starch | 55.0 | 55.0 | 55.0 | 55.0 |
| 4. Lactose | 167.4 | 166.5 | 212.5 | 257.5 |
| 5. Dioctyl Sodium Sulfosuccinate | 1.5 | 1.5 | 1.5 | 1.5 |
| 6. Talc | 5.0 | 5.0 | 5.0 | 5.0 |
| 7. Magnesium Stearate | 1.0 | 1.0 | 1.0 | 1.0 |
| Capsule Fill Weight | 250 mg. | 250 mg. | 300 mg. | 350 mg. |

Procedure:
1. Mix items 1, 3 and 5 in a suitable mixer.
2. Dissolve items 2 and 5 in distilled water and/or alcohol and granulate to proper consistency. Mill.
3. Dry in a suitable oven.
4. Mill and mix with talc and magnesium stearate for 3 minutes.
5. Encapsulate on suitable machine.

TABLET FORMULATION:-(Wet Granulation)

| | mg/tablet | mg/tablet | mg/tablet | mg/tablet |
|---|---|---|---|---|
| 1. Bromolasalocid | 0.1 | 1 | 5 | 10 |
| 2. Lactose | 202.9 | 202 | 232 | 261 |
| 3. Modified Starch | 25 | 25 | 35 | 45 |
| 4. Pregelatinized Starch | 20 | 20 | 25 | 30 |
| 5. Distilled Water q.s. | — | — | — | — |
| 6. Magnesium Stearate | 2 | 2 | 3 | 4 |
| Weight of Tablet | 250 mg. | 250 mg. | 300 mg. | 350 mg. |

Procedure:
1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 4

A test was conducted for antihypertensive activity in the DOCA Na rat utilizing low dose chronic administration.

DOCA Na male rats weighing 170 to 210 grams are used in the test. DOCA Na hypertension is induced by unilateral nephrectomy followed by subcutaneous implantation of a 25 mg. desoxycorticosterone (DOCA) pellet. Animals are placed in individual cages receiving 0.9% sodium chloride solution to drink and rat chow diet ad libitum. Two weeks are allowed to elapse from the time of surgery for development of hypertension, i.e., systolic blood pressure of at least 150 mmHg.

Mean blood pressure and heart rate in the rats dosed at 5 mg/kg/day, 1 mg/kg/day, 0.1 mg/kg/day and as those used as controls are measured directly by placing a polyethylene catheter in a femoral artery and thereafter measuring the blood pressure by a Stathem Pressure Transducer. Control animals and drug dosed subjects are measured side by side. Direct readings were taken when the animal model began to show signs of inherent deterioration.

The experimental results are represented as absolute values. Drug-related alterations in mean blood pressure are expressed as percentage change by comparing control absolute values with drug absolute values. Compounds are considered active when about a 15% or greater reduction in blood pressure is obtained. However, the reduction in blood pressure must show mathematical significance ($p < 0.5$).

A derivative of the polyether ionophore, laslaocid, i.e., the bromo derivative of lasalocid, was tested in the above screen. The compound was administered in a food admix on a daily basis. The results are summarized as follows:

TABLE IV

| Parameter | Control Mean Value | 0.1 mg/kg/day at 24 Days | % Δ | 1 mg/kg/day at 28 Days | % Δ | 5 mg/kg/day at 11 Days | % Δ |
|---|---|---|---|---|---|---|---|
| Arterial blood pressure | 175.0±3.8 | 132.4±16.0 | −24.34 | 140.1±16 | −19.94 | 140.0±12.6 | −20.00 |
| Pulse pressure | 62.5±5.3 | 41.1±7.4 | −34.24 | 45±3.5 | −28.00 | 47.4±7.3 | −24.16 |
| Stroke Volume Index | 4.82±0.31 | 4.03±0.17 | −16.39 | 5.86±.31 | 21.58 | 4.96±0.61 | 2.90 |

As seen from the above Table, both pulse pressure and blood pressure are lowered following chronic administration of bromolasalocid. The stroke volume index which is a measure of the amount of blood pumped indicates that no significant alteration has occurred and that pump performance is competent, i.e., that the myocardium has not been compressed.

We claim:

1. A method for treating hypertension in warm blooded animals with hypertension comprising the oral administration to such warm blooded animals of from less than 0.1 mg/kg/day to about 10 mg/kg/day of a polyether compound with ionophore activity.

2. The method of claim 1 wherein the dose administered is from about 5 mg/kg/day to about 10 mg/kg/day.

3. The method of claim 1 wherein the dose administration is chronic and is from less than 0.1 mg/kg/day to about 5 mg/kg/day.

4. The method of claim 1 wherein said compound is bromolasalocid.

5. The method of claim 1 wherein said compound is monensin.

6. The method of claim 1 wherein said compound is A23187.

7. The method of claim 1 wherein said compound is A204.

8. The method of claim 1 wherein said compound is X-206.

9. The method of claim 1 wherein said compound is bromoisolasalocid A.

10. The method of claim 1 wherein said compound is Nigericin.

11. The method of claim 1 wherein said compound is A-130A.

12. The method of claim 1 wherein said compound is Lysocellin.

13. The method of claim 1 wherein said compound is BL-580.

14. A method of altering the hemodynamic profile of warm blooded animals suffering from angina to the normal state comprising orally administering to such warm blooded animals from less than 0.1 mg/kg/day to about 10 mg/kg/day of a polyether compound with ionophoric activity sufficient to revert the hemodynamic profile to the normal state.

15. The method of claim 14 wherein the dose administered is from about 5 mg/kg/day to about 10 mg/kg/day.

16. The method of claim 14 wherein the dose administration is chronic and is from less than 0.1 mg/kg/day to about 5 mg/kg/day.

17. The method of claim 14 wherein said compound is bromolasalocid.

18. The method of claim 14 wherein said compound is A 23187.

19. The method of claim 14 wherein said compound is monensin.

20. The method of claim 14 wherein said compound is BL-580.

* * * * *